United States Patent
Parker

(10) Patent No.: US 9,453,908 B2
(45) Date of Patent: Sep. 27, 2016

(54) SUPERRESOLUTION IMAGING OF SCATTERERS IN PULSE-ECHO IMAGING

(75) Inventor: Kevin J. Parker, Rochester, NY (US)

(73) Assignee: University of Rochester, Rochester, NY (US)

( * ) Notice: Subject to any disclaimer, the term of this patent is extended or adjusted under 35 U.S.C. 154(b) by 0 days.

(21) Appl. No.: 13/494,538

(22) Filed: Jun. 12, 2012

(65) Prior Publication Data
US 2013/0331698 A1 Dec. 12, 2013

(51) Int. Cl.
*A61B 8/00* (2006.01)
*G01S 7/52* (2006.01)
*A61B 8/08* (2006.01)
*G01S 15/89* (2006.01)

(52) U.S. Cl.
CPC .......... *G01S 7/52047* (2013.01); *A61B 8/0883* (2013.01); *A61B 8/5207* (2013.01); *G01S 15/8977* (2013.01)

(58) Field of Classification Search
CPC .......... A61B 8/08; A61B 8/58; A61B 8/587; G06K 9/00516
USPC .......... 600/407, 437, 443; 382/128
See application file for complete search history.

(56) References Cited

U.S. PATENT DOCUMENTS

| | | | |
|---|---|---|---|
| 3,805,596 A * | 4/1974 | Klahr | A61B 8/08 367/7 |
| 6,542,626 B1* | 4/2003 | Brouwer et al. | 382/128 |
| 2004/0054281 A1* | 3/2004 | Adam et al. | 600/437 |
| 2009/0088638 A1* | 4/2009 | Sato et al. | 600/443 |
| 2011/0033098 A1* | 2/2011 | Richter et al. | 382/131 |

OTHER PUBLICATIONS

Healey et al (A complex Z-transform technique for speckle reduction).*
Rasmussen (Maximum likelihood estimation of the parameters of nonminimum phase and noncausal ARMA models).*

* cited by examiner

*Primary Examiner* — Joel F Brutus
(74) *Attorney, Agent, or Firm* — Riverside Law LLP

(57) ABSTRACT

In ultrasound B-scan imaging or other pulse-echo imaging, an inverse filter solution eliminates both the speckle phenomenon and the poor resolution dependency on the pulse length and width to produce SURUS (super-resolution ultrasound) images. The pulse shapes have stable inverses, derived by use of the standard Z-transform and related properties.

15 Claims, 14 Drawing Sheets

Gaussian Pulse

Inverse Filter

Figure 3A
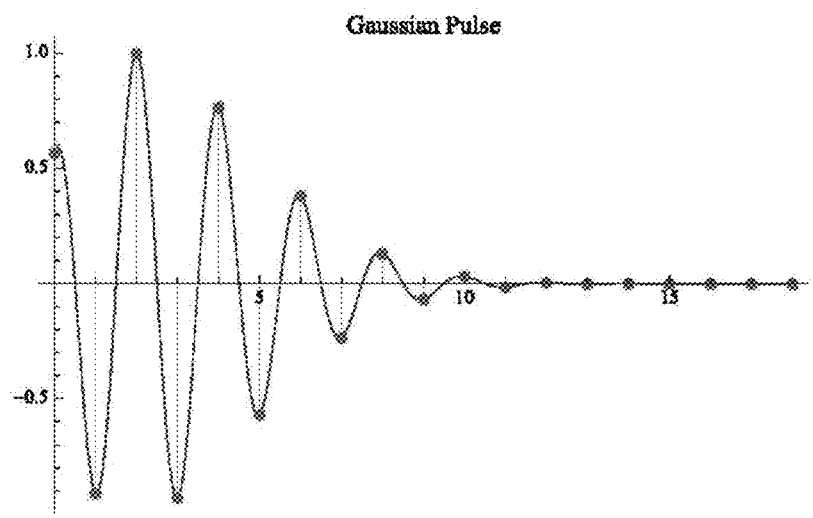
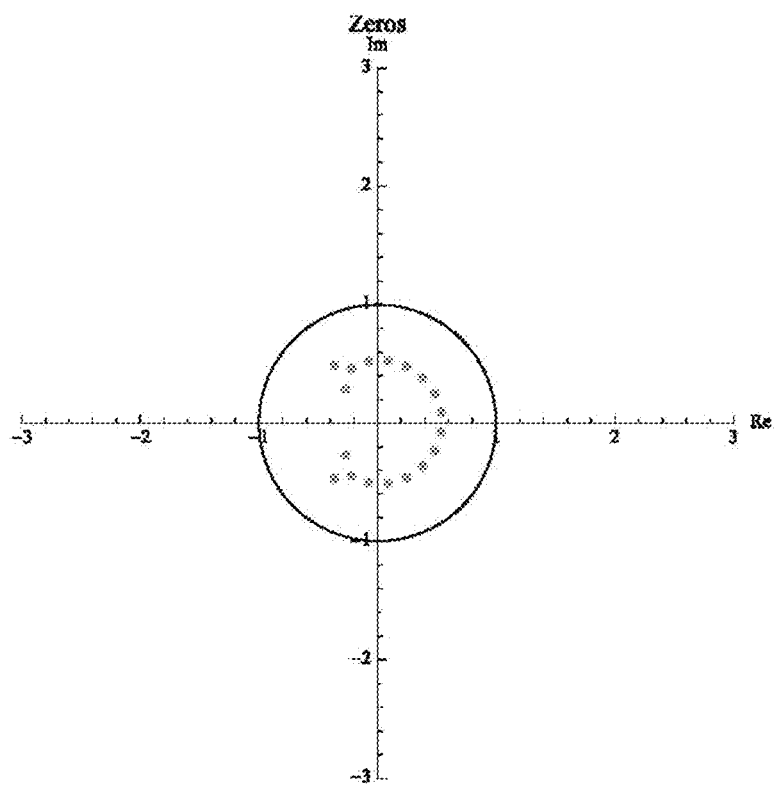
Figure 3B

Figure 4B
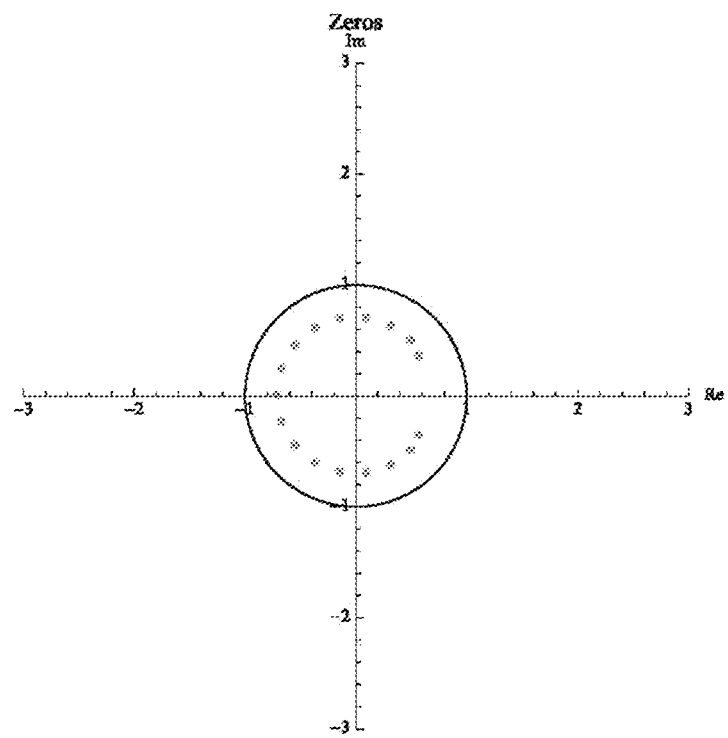
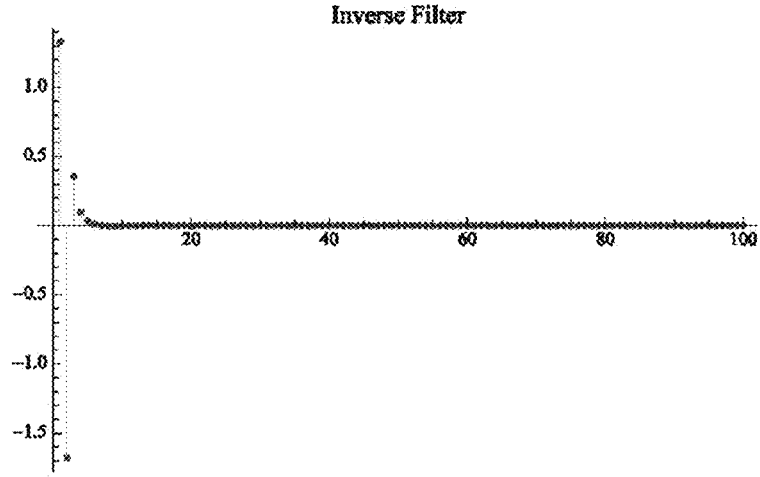
Figure 4C

Figure 5
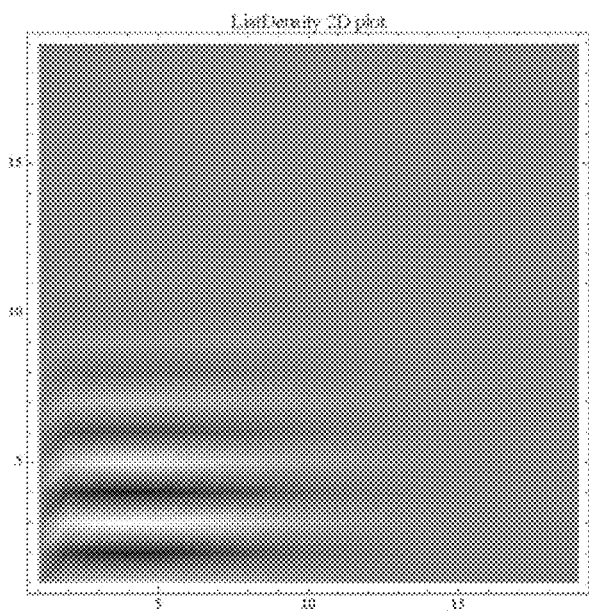
Figure 6A       Figure 6B
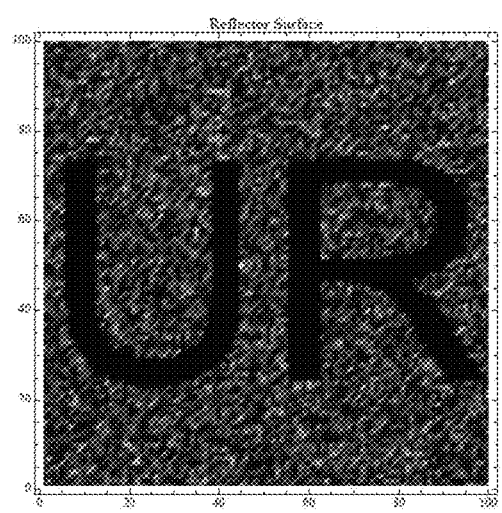       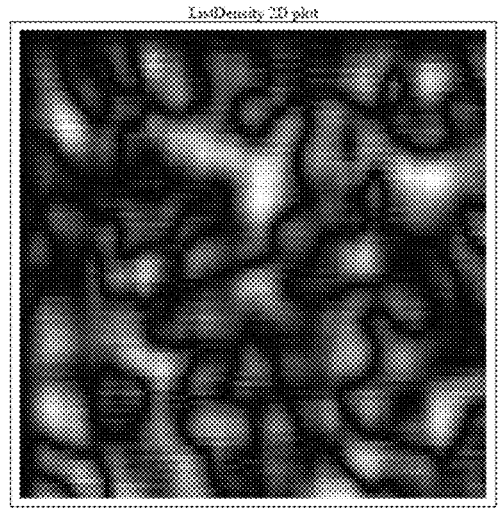

Figure 6C
Figure 6D
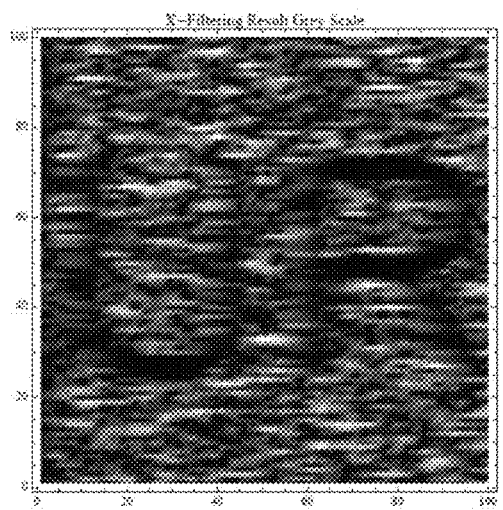
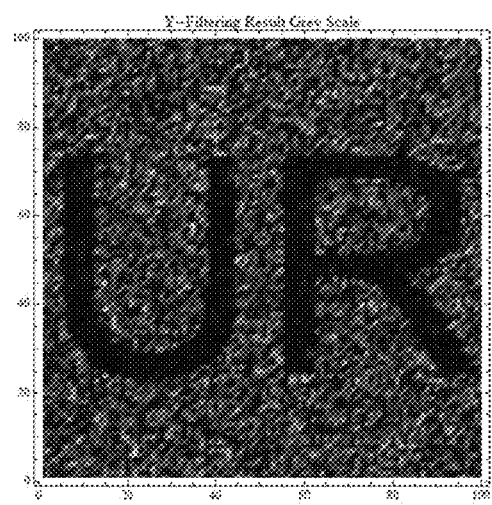
Figure 7A
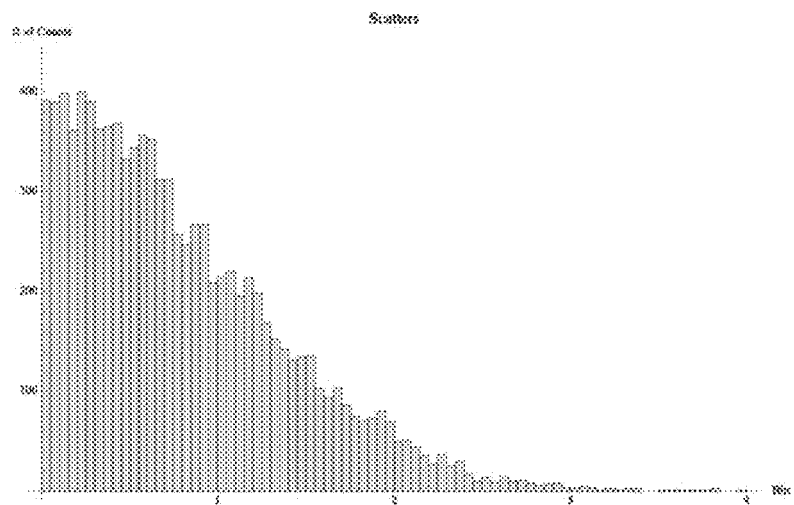

Figure 11A
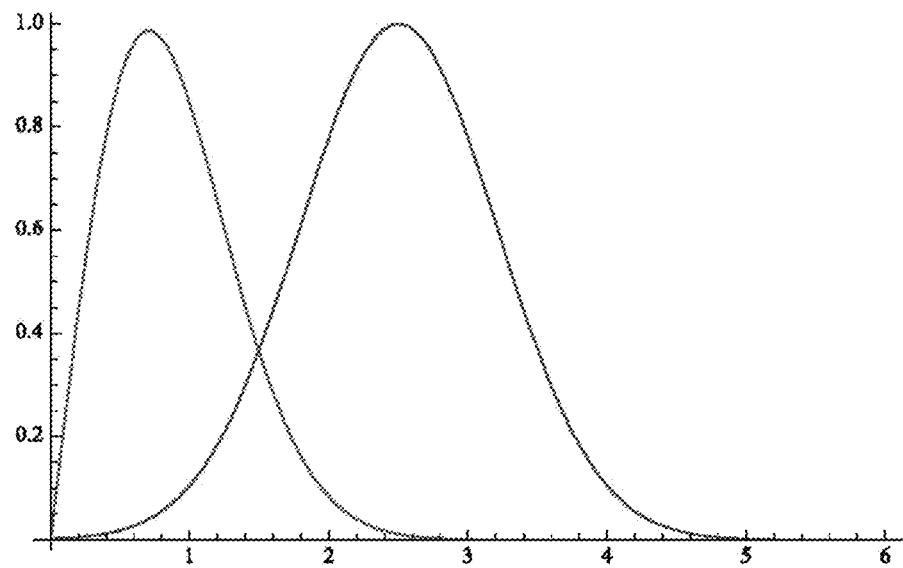
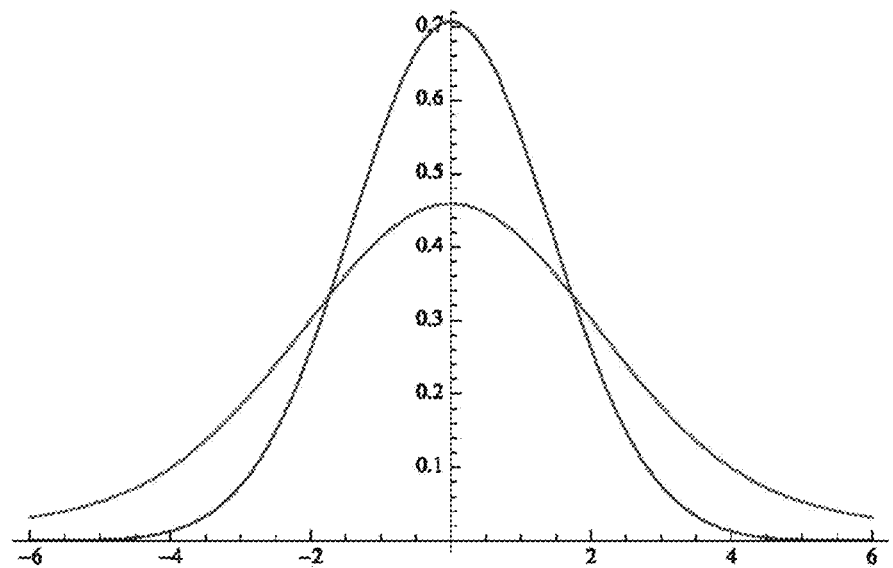
Figure 11B

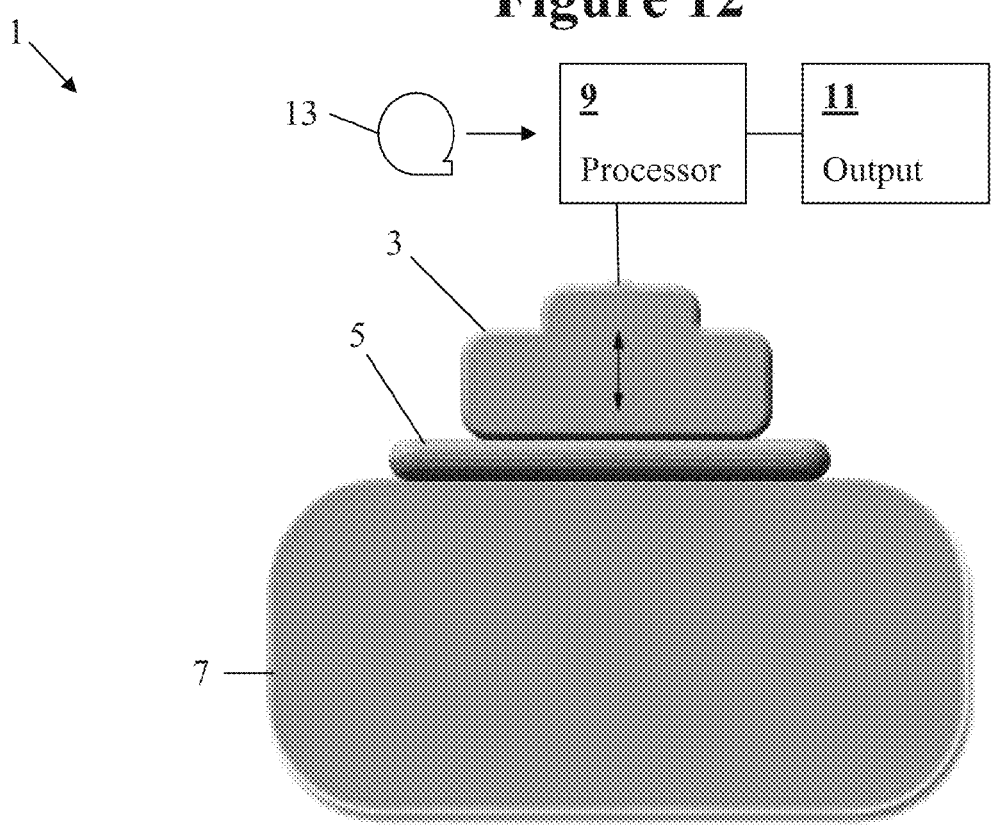

SUPERRESOLUTION IMAGING OF SCATTERERS IN PULSE-ECHO IMAGING

FIELD OF THE INVENTION

The present invention is directed to pulse-echo imaging, such as ultrasound imaging, and more particularly to such imaging that uses a transform to achieve superresolution.

DESCRIPTION OF RELATED ART

At the heart of analytical models of pulse-echo imaging is an integration on the product of the propagating pulse and the reflectors or scatterers, over the location of the pulse at some point in time (Macovski 1983; Szabo 2004; Prince and Links 2006). Under a number of approximations and simplifications about attenuation and diffraction, the integration can be reduced to a convolution model (Macovski 1983) such that the received echo e(t) is approximated by:

$$e(t) = A\left\{p(t)s(x,y) * * * R\left(x, y, \frac{ct}{2}\right)\right\} \quad (1)$$

where A is an amplitude constant, p(t) is the propagating pulse in the axial direction, s(x,y) is the beam width in the transverse and elevational axes (and thus the beam pattern is assumed to be a separable function), and R(x,y,z) is the 3D pattern of reflectors or scatterers. The speed of sound is c, and with a round trip for the echo the axial distance z is replaced by $$\frac{ct}{2}$$

in the 3D convolution represented by the symbol ***. The problems of poor resolution and speckle can be understood as a direct result of this convolution. The spatial resolution is set by the full spatial extent of the propagating pulse in 3D, which is typically many multiples of a wavelength. However, in tissue, small scatterers at the cellular level and micro-structural level such as the arterioles and capillaries will have a dimensions on the order of 10 microns, much smaller than typical pulse shapes (the wavelength at 10 Mhz is 150 microns, for example, and the pulse length will be multiples of this). With many subresolvable scatterers interacting with a propagating pulse, the resulting echo will exhibit the random constructive and destructive interference pattern known as speckle (Burckhardt 1970; George and Jain 1973; George et al. 1976; Burckhardt 1978; Wagner et al. 1983; Tuthill et al. 1988; Reynolds et al. 1989). The problems with a visual interpretation of speckle images are profound, since the patterns of nulls and peaks may or may not correspond to actual nulls or peaks of the scatterers, but rather to their summation over the positive and negative portions of the propagating pulse. Furthermore, the lesion detection problem is made more difficult by the overlap of Rayleigh statistics from different distributions of a lesion and a background (Sperry and Parker 1991; Cramblitt and Parker 1999). Attempts to improve the situation include speckle reduction algorithms (Bamber 1993) and deconvolution approaches (Jensen 1992; Alam et al. 1998; Haider et al. 1998; Taxt and Frolova 1999; Qinzhen et al. 2003; Michailovich and Adam 2004; Kerner and Porat 2008; Shin et al. 2010). Despite all these attempts, the typical medical ultrasound image still retains the two characteristic elements of resolution limited by the pulse size and shape, and speckle statistics. There are reasons to suspect that this is an intractable problem. The spectrum of a typical pulse is a band-pass signal, so the DC, very low frequency, and very high frequency components of the reflectors are not captured. This limits the amount of "whitening" or equalization that can be accomplished. From a 2D imaging point of view, the illumination of k-space by a typical pulse is a discouragingly small area of support, constraining the strategies for improving image quality while reducing speckle (Munson and Sanz 1984).

Throughout the present disclosure, reference will be made to the following references, which are hereby incorporated by reference in their entireties into the present disclosure:

Alam S K, Ophir J, Cespedes I, Varghese T. A deconvolution filter for improvement of timedelay estimation in elastography. Ieee T Ultrason Ferr 1998; 45:1565-72.

Bamber J C. Speckle reduction. In: ed. Advances in ultrasound techniques and instrumentation. New York: Churchill Livingstone, 1993. pp. 55-67.

Burckhardt C B. Laser speckle pattern—a narrowband noise model. Bell Sys Tech J 1970; 49:309-16.

Burckhardt C B. Speckle in Ultrasound B-Mode Scans. Ieee T Son Ultrason 1978; 25:1-6.

Cramblitt R M, Parker K J. Generation of non-Rayleigh speckle distributions using marked regularity models. Ieee T Ultrason Ferr 1999; 46:867-74.

George N, Christensen C R, Bennett J S, Guenther B D. Speckle Noise in Displays. J Opt Soc Am 1976; 66:1282-90.

George N, Jain A. Speckle Reduction Using Multiple Tones of Illumination. Appl Optics 1973; 12:1202-12.

Haider B, Lewin P A, Thomenius K E. Pulse elongation and deconvolution filtering for medical ultrasonic imaging. Ieee T Ultrason Ferr 1998; 45:98-113.

Jackson L B. Signals, systems, and transforms. In: ed. Addison-Wesley series in electrical engineering. Reading, Mass.: Addison-Wesley, 1991. pp. pp. 59-136.

Jensen J A. Deconvolution of ultrasound images. Ultrason Imaging 1992; 14:1-15.

Kerner Y, Porat M. Acoustic imaging using a maximum likelihood approach. Direct and Inverse Problems of Electromagnetic and Acoustic Wave Theory, 2008 DIPED 2008 13$^{th}$ International Seminar/Workshop on, 2008; 163-7.

Macovski A. Basic Ultrasonic Imaging. In: ed. Medical Imaging Systems. Englewood Cliffs, N.J.: Prentice-Hall, 1983. pp. 173-203.

Michailovich O, Adam D. Phase unwrapping for 2-D blind deconvolution of ultrasound images. IEEE Trans Med Imaging 2004; 23:7-25.

Munson D C, Sanz J L C. Image-Reconstruction from Frequency-Offset Fourier Data. P Ieee 1984; 72:661-9.

Oppenheim A V, Schafer R W. Digital signal processing. In: ed. Englewood Cliffs, N.J.: Prentice-Hall, 1975. pp. pp. 45-86.

Prince J L, Links J M. Ultrasound imaging systems. In: ed. Medical Imaging Signals and Systems. Upper Saddle River, N.J.: Pearson Prentice Hall, 2006. pp. 347-78.

Qinzhen X, Suiren W, Wenjiang P, Luxi Y. Ultrasonic image processing using wavelet based deconvolution. Neural Networks and Signal Processing, 2003 Proceedings of the 2003 International Conference on, 2003; 1013-6 Vol. 2.

Reynolds G O, DeVelis J B, Parrent G B, Thompson B J. Sources of coherent noise and their reduction. In: ed. The New Physical Optics Notebook: Tutorials in Fourier Optics. New York: American Institute of Physics, 1989. pp. 199-219.

Shin H C, Prager R, Gomersall H, Kingsbury N, Treece G, Gee A. Estimation of average speed of sound using deconvolution of medical ultrasound data. Ultrasound Med Biol 2010; 36:623-36.

Sperry R H, Parker K J. Segmentation of speckle images based on level-crossing statistics. J Opt Soc Am A 1991; 8:490-8.

Szabo T L. Wave scattering and imaging. In: ed. Diagnostic Ultrasound Imaging: Inside Out. Amsterdam; Boston: Elsevier Academic Press, 2004. pp. 213-42.

Taxt T, Frolova G V. Noise robust one-dimensional blind deconvolution of medical ultrasound images. IEEE Trans Ultrason Ferroelectr Freq Control 1999; 46:291-9.

Tuthill T A, Sperry R H, Parker K J. Deviations from Rayleigh statistics in ultrasonic speckle. Ultrason Imaging 1988; 10:81-9.

Wagner R F, Smith S W, Sandrik J M, Lopez H. Statistics of Speckle in Ultrasound B-Scans. Ieee T Son Ultrason 1983; 30:156-63.

SUMMARY OF THE INVENTION

It will thus be seen that a need exists in the art to improve image quality in pulse-echo imaging. It is therefore an object of the invention to provide such an improvement.

To achieve the above and other objects, the present invention is directed to an approach to an inverse filter solution with stabilized ultrasound pulses. Stabilized pulses, in this context, are realizable continuous functions in the axial and transverse directions that when sampled have their Z-transform zeroes lying within the unit circle. This corresponds to inverse filters that are stable because their poles lie within the unit circle, such that they are limited in time with bounded output. By applying an exact, stable inverse filter, the final result is a very high resolution, subwavelength solution to the distribution of scatterers that were previously below the resolution of the ultrasound pulse and the imaging system. The integration of random scatterers over the pulse length and width is essentially disaggregated by the inverse filter operation. Therefore, the two dominant and problematic system effects of pulse length and speckle statistics are eliminated, replaced by a more favorable and high resolution calculation of the distribution of scatterers within tissue. The solution is exact within the framework of the convolution model and sampled signals, yet is approximate in the sense that the sampling frequency (nominally twice the center frequency of the transmit pulse in simple examples) will result in aliasing of any signal above the Nyquist frequency. The solutions are also accurate with respect to the physical reality to the extent that the convolution model is accurate and the effect of noise is limited. The resulting images are termed SURUS images, as they are super-resolution ultrasound images.

BRIEF DESCRIPTION OF THE DRAWINGS

A preferred embodiment of the present invention will be set forth in detail with reference to the drawings, in which:

FIG. 3A is a plot showing another modification of the pulse shape of FIG. 1A in accordance with the preferred embodiment;

FIG. 3B is a plot showing the Z-transform of the pulse shape of FIG. 3A;

FIG. 4B is a plot showing the Z-transform of the sampled transverse beam pattern of FIG. 4A;

FIG. 4C is a plot showing the inverse filter corresponding to the sampled transverse beam pattern of FIG. 4A;

FIG. 5 is a plot showing the combined pulse in two dimensions;

FIG. 6A is an image showing a reflector surface used to test the preferred embodiment;

FIG. 6B is an image reconstructed from the reflector surface of FIG. 6A before inverse filtering;

FIG. 6C is an image showing the result of convolution of the image of FIG. 6B with the axial inverse filter;

FIG. 6D is an image showing the result of convolution of the image of FIG. 6C with the transverse inverse filter;

FIGS. 7A-7C are plots showing the scatters, the echo, and the deconvolution result, respectively;

FIG. 11A is a plot showing two pulses;

FIG. 11B is a plot showing the Fourier transforms of the two pulses; and

FIG. 12 is a block diagram showing a system on which the preferred embodiment can be implemented.

DETAILED DESCRIPTION OF THE PREFERRED EMBODIMENT

Figure 1A:
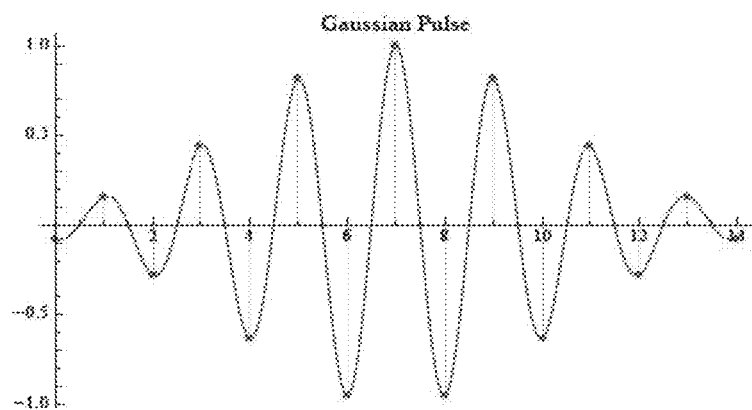
FIG. 1A is a plot showing a conventional pulse shape.

A preferred embodiment will now be set forth in detail with reference to the drawings, in which like reference numerals refer to like elements or steps throughout.

We begin with a discrete version of Equation (1) with the inclusion of noise. Without loss of generality, the 2D version is given as:

$$e[n]=p[n]s[m]**R[n,m]+g[n,m] \quad (2)$$

where $g[n,m]$ is additive noise.

The objective is to reconstruct the scatterers or reflectors $R[n,m]$. For this we turn to the Z-transform of $p[n]$. The one-sided Z-transform of $p[n]$ is given by (Oppenheim and Schafer 1975):

$$P(z) = \sum_0^\infty p[n]z^{-n} \quad (3)$$

For a pulse of length N, the Z-transform is a polynomial of order N−1, which can be factored into roots, giving zeros of the Z-transform. The inverse filter, given by the transform $1/P(z)$, will convolve with $p[n]$ to produce an impulse. However, it is clear that the reciprocal nature of $P(z)$ and its inverse filter transform implies that the zeroes of the pulse transform $P(z)$ become the poles of the inverse filter. Generally, for a causal, right-handed system to be stable, the poles of the Z-transform must lie within the unit circle and the region of convergence includes the unit circle. This is analogous to poles of a stable system lying in the left half plane for Laplace transforms. With poles on or outside the unit circle, the impulse response of these systems would be unstable and unbounded.

Assuming that a stable inverse filter $1/P(z)$ can be derived, with an impulse response of $p^{-1}[n]$, then a convolution of the received echo with the inverse filter yields:

$$p^{-1}[n]*e[n]=p^{-1}[n]*p[n]*R[n]+p^{-1}[n]*g[n] \quad (4)$$

where the one-dimensional form of Equation (2) is used for simplicity. Also, by definition, $$p^{-1}[n]*p[n]=\delta[n] \quad (5)$$

where $\delta[n]$ is the discrete delta function, so that $$p^{-1}[n]*e[n]=\delta[n]*R[n]+p^{-1}[n]*g[n]=R[n]+p^{-1}[n]*g[n] \quad (6)$$

In the absence of noise, the use of the inverse filter yields $R[n]$ exactly, a high resolution replica of the sampled scatter function. Given noise, the stability and frequency response of $p^{-1}[n]$ must be considered to minimize the term $p^{-1}[n]*g[n]$.

Thus far we considered the general case of a one-dimensional signal $p[n]$ and its Z-transform. Since our imaging pulse is two (or three) dimensional, we need to consider a two (or three) dimensional Z-transform. However, since the convolutional model has separable functions for axial and transverse dimensions, then the 2D Z-transform reduces to separable functions as well.

The problem, therefore, is to find and apply inverse filters for $p[n]$ and $s[m]$. Unfortunately, the typical ultrasound pulses used for imaging are functions that, when sampled, have Z-transforms with many zeroes on and outside of the unit circle (see Michailovich and Adam (2004) for examples). These produce inverse filters with poles outside of the unit circle, leading to unstable filters. Further examples are given below.

One way to create stabilized pulses (meaning pulses that, when sampled, possess stable inverse filters) is to multiply $p[n]$ by the quantity $\beta^n$, where $\beta$ is a real number<1. In the discrete world, if a right-sided sequence $p[n]$ with a Z-transform $P[Z]$ is multiplied by an exponential sequence $\beta^n$, then (Oppenheim and Schafer 1975; Jackson 1991):

$$Z[\beta^n p[n]]=P(z/\beta) \quad (7)$$

Thus the multiplication by a geometric series creates an asymmetric pulse in the time domain with its Z-transform zeroes "retracted" into the unit circle depending on the factor beta. A similar consideration applies to samples of the transverse beam function $s[m]$, and examples are provided below.

Results will now be set forth.

Figure 1B:
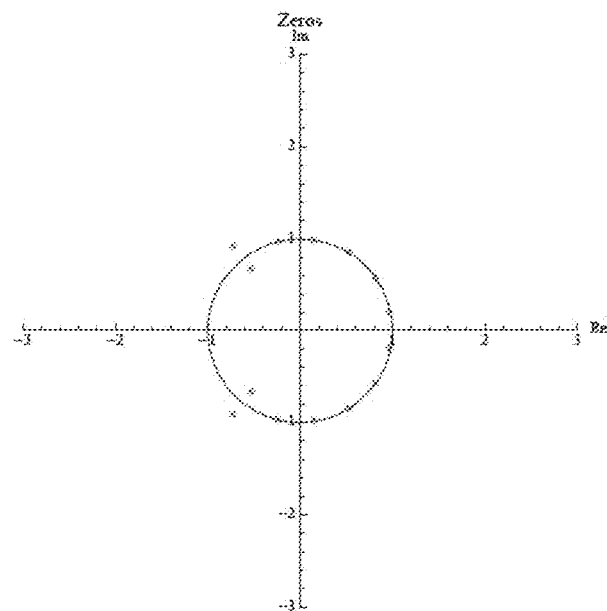
FIG. 1B is a plot showing the Z-transform of the pulse shape of FIG. 1A.

First, we examine a conventional pulse shape $p[t]$, shown in FIG. 1A, which is modeled as a Gaussian envelope modulated by a cosine at the center frequency of the transducer. The continuous function is sampled at twice the center frequency and 15 points are taken as $p[n]$. The Z-transform of this sampled pulse, shown in FIG. 1B, has numerous zeroes on the unit circle and a pair of conjugate zeroes outside of the unit circle.

Figure 2A:
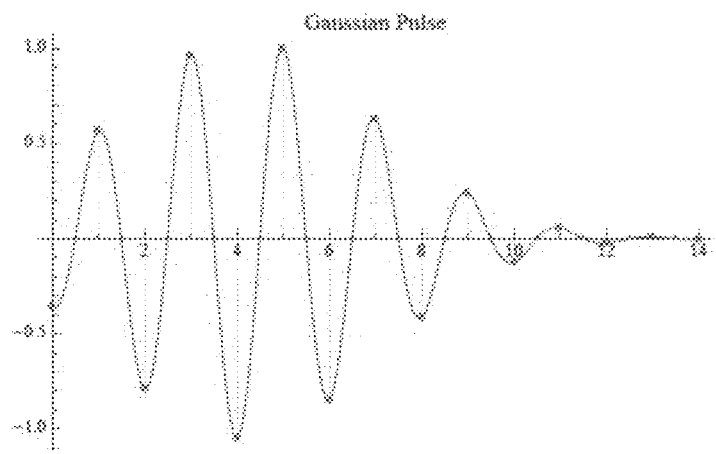
FIG. 2A is a plot showing a modification of the pulse shape of FIG. 1A in accordance with the preferred embodiment.
Figure 2B:
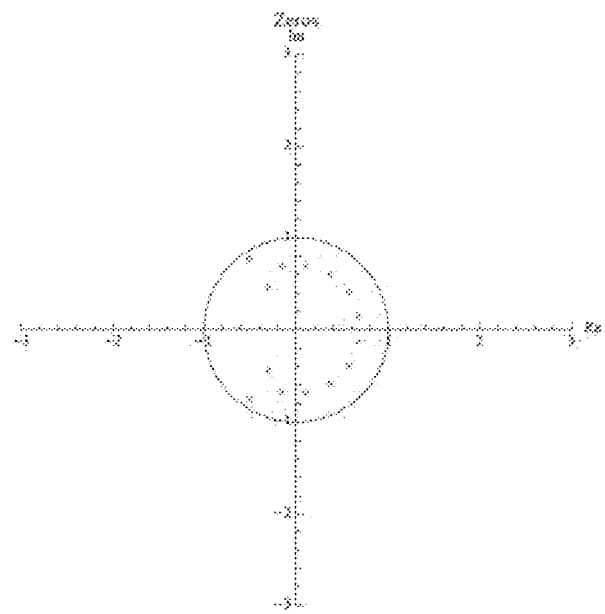
FIG. 2B is a plot showing the Z-transform of the pulse shape of FIG. 2A.

These zeroes will become poles of the inverse filter, and signify an unstable, unbounded output result. Therefore, this class of typical pulse echo shape is not conducive to inverse filters. However, by modifying the function with a geometric series, a beta term in Equation (7), the pulse can be made asymmetric, and the inverse transform is stabilized. As an example, the Gaussian function in the preceding figure is multiplied by $0.7^n$. The pulse and its Z-transform are shown in FIGS. 2A and 2B, respectively.

Now all the zeroes of the transform lie within the unit circle. Accordingly, the inverse filter will have poles within the unit circle and will have a bounded input/bounded output impulse response of limited duration.

In general, we have found that the formation of a stabilized pulse is not restricted to the use of a $\beta^n$ type function; rather this is illustrative of envelopes that have a sharp initial rise and a more gradual fall-off from the peak. We call these "asymmetric" envelopes or pulses, and these can be characterized by a number of different analytic functions. One example is a piecewise exponential rise with one time constant and then an exponential fall with a longer time constant. Another example for a pulse is a Gaussian function in time multiplied by a sine or cosine, as in conventional modulation, but with a step function at t=0 and multiplied by t:

$$p(t)=\sin(\omega t+\phi)*\sqrt{t}*e^{[(t-\upsilon)^2/2\sigma^2]}*\text{UnitStep}(t) \quad (8)$$

Figure 3C:
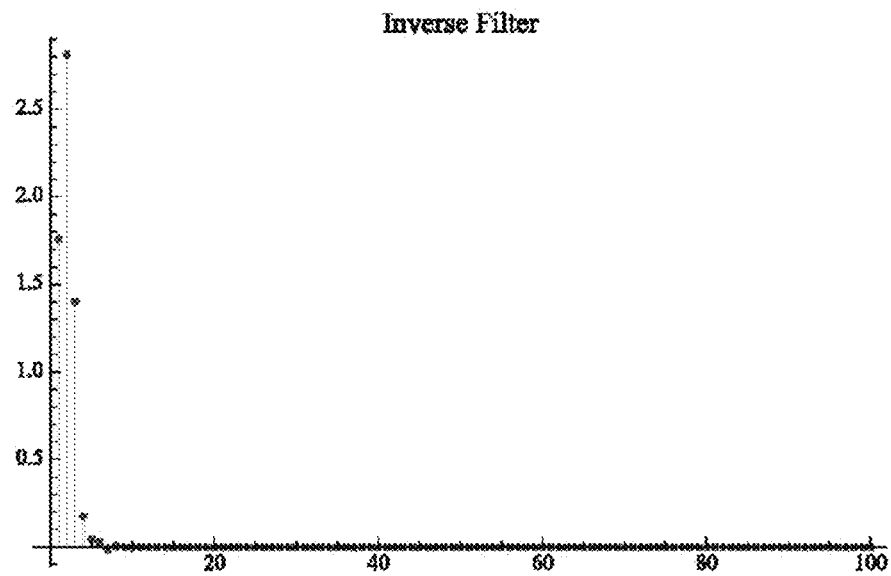
FIG. 3C is a plot showing the inverse filter corresponding to the pulse shape of FIG. 3A.

This produces an asymmetric envelope similar to a Rayleigh distribution function. When sampled at twice the modulation frequency, and aligned to the peaks of the function, the resulting sampled $p[n]$, and its pole-zero diagram, and its inverse filter are shown in FIGS. 3A-3C respectively.

For the transverse beam pattern $s(x)$, we choose the asymmetric function:

$$s(x)=x*e^{[-x^2/2\sigma x]}*\text{UnitStep}(x) \quad (9)$$

Figure 4A:
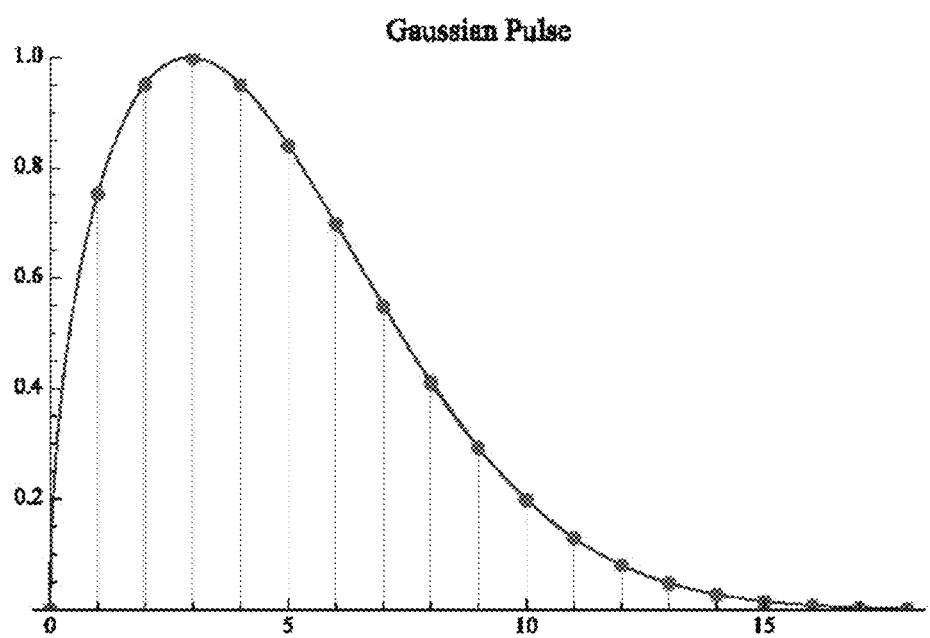
FIG. 4A is a plot showing a sampled transverse beam pattern according to the preferred embodiment.

The sampled version, $s[m]$, is given in FIG. 4A, along with the corresponding pole-zero diagram and the inverse filter result in FIGS. 4B and 4C, respectively. The rapid decay of this inverse filter, along with the inverse of $p[n]$, is quite beneficial to the suppression of noise.

The combined pulse $p[n]s[m]$ in two dimensions is shown in FIG. 5, and its non-symmetry is readily apparent.

The pulse shown in FIG. 5 is used to image a field of random scatterers, with a pattern of letter-shaped nulls running through the field, shown in FIG. 6A. The conventional speckle pattern results, as shown in FIG. 6B, and the null characters cannot be discerned. After convolution with axial (vertical) and transverse (horizontal) inverse filters, as shown in FIGS. 6C and 6D respectively, the original pattern is reproduced exactly except for the effects of 5% rms noise added to the original signal before inverse filtering.

Figure 7B:
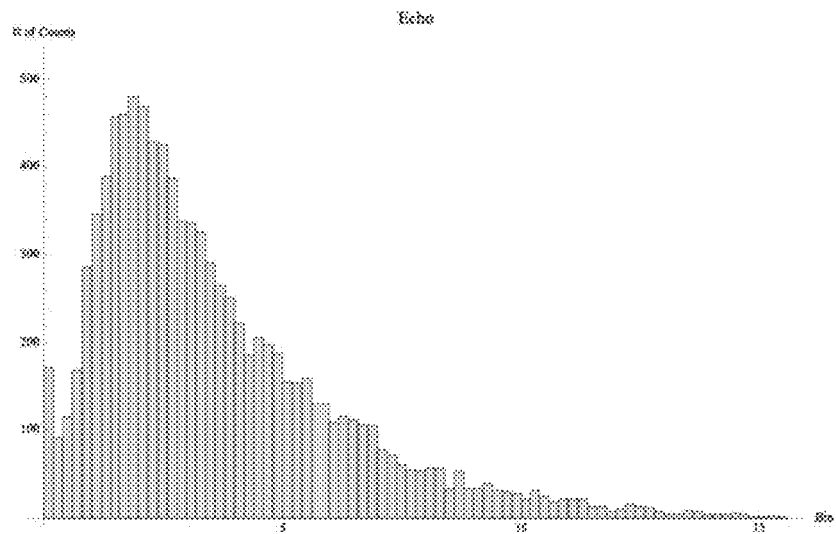
Figure 7C:
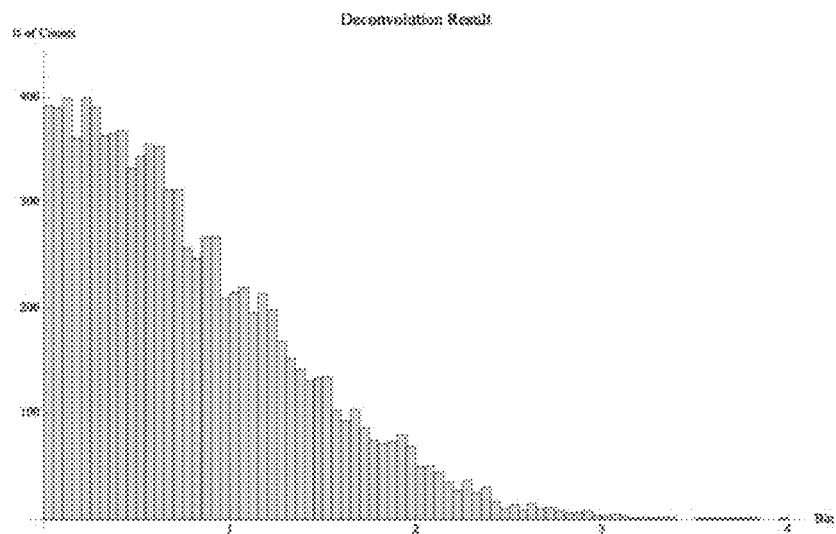

From the visual appearance, the speckle pattern has been converted to a fine-grain scatterer map. Statistically, the unfavorable Rayleigh statistics of speckle are converted into the statistics of the scatterers. That is demonstrated in FIGS. 7A-7C. Plotted are the histograms of the absolute value of the original scatterers (FIG. 7A), the envelope of the echo demonstrating Rayleigh statistics (FIG. 7B), and the absolute value of the echo after filtering (FIG. 7C). The original Gaussian distribution of the scatterers has been restored.

Figure 8A:
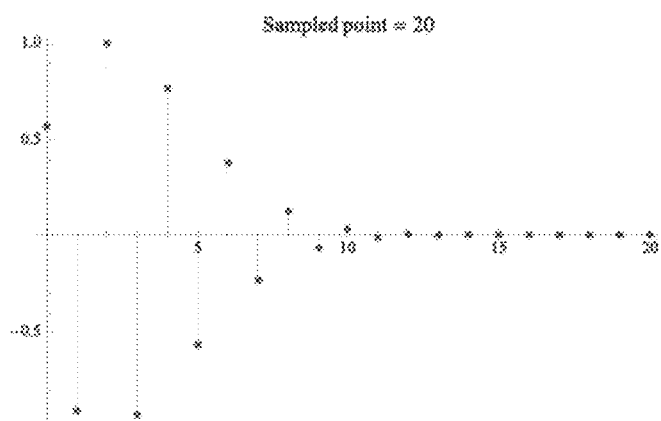
FIG. 8A is a plot showing a pulse sampled at exactly twice the modulation frequency.
Figure 8B:
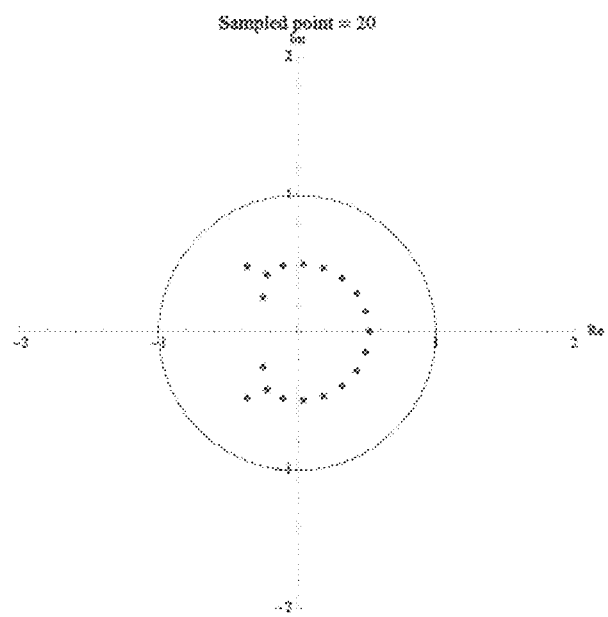
FIG. 8B is a plot showing the Z-transform of the pulse of FIG. 8A.
Figure 9A:
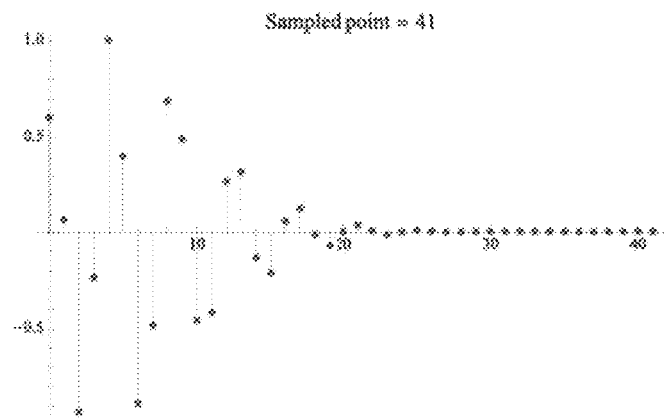
FIG. 9A is a plot showing a pulse sampled at double the sampling rate of FIG. 8A.
Figure 9B:
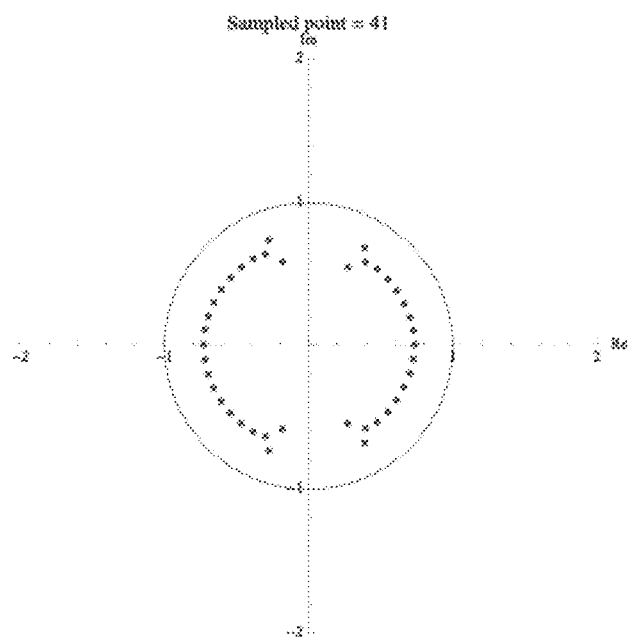
FIG. 9B is a plot showing the Z-transform of the pulse of FIG. 9A.
Figure 9C:
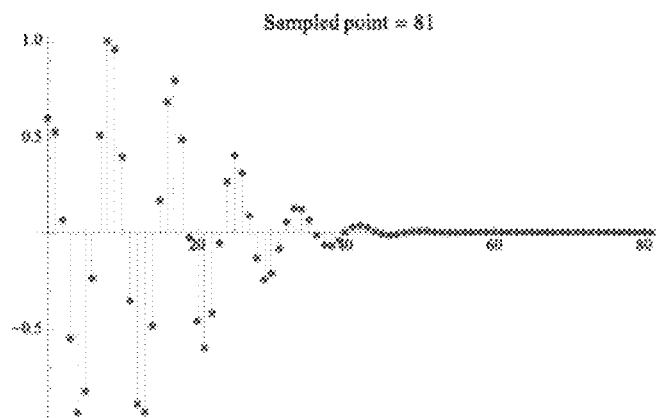
FIG. 9C is a plot showing a pulse sampled at double the sampling rate of FIG. 9A.
Figure 9D:
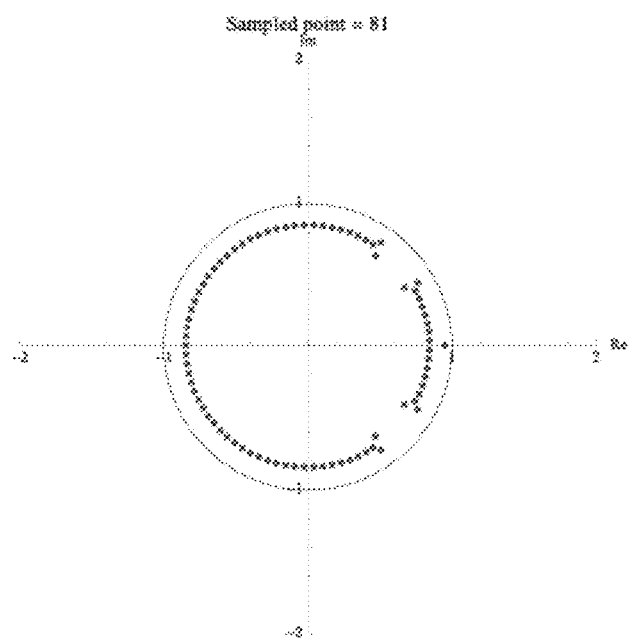
FIG. 9D is a plot showing the Z-transform of the pulse of FIG. 9C.
Figure 10A:
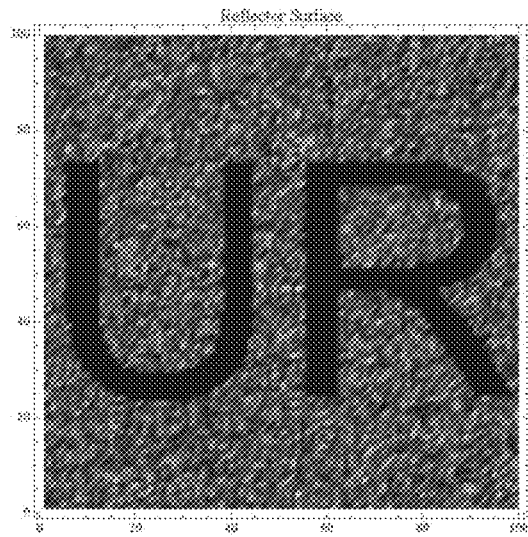
FIG. 10A is an image showing a reflector surface used in testing an inverse filter with an incorrect value of β.
Figure 10B:
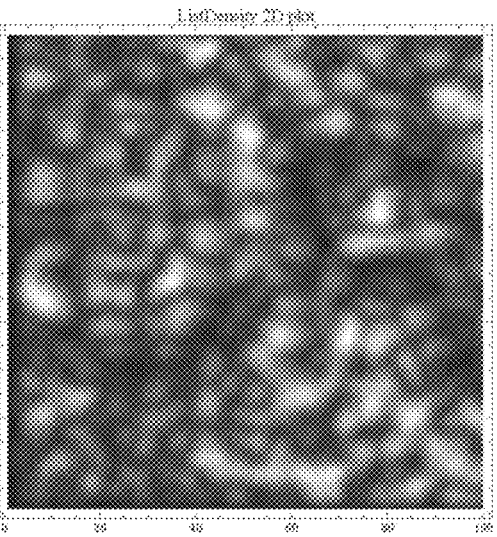
FIG. 10B is an image reconstructed from the reflector surface of FIG. 10A before inverse filtering.
Figure 10C:
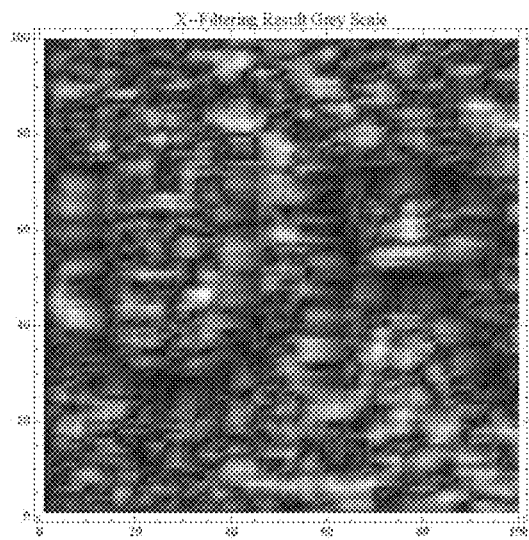
FIG. 10C is an image showing the result of convolution of the image of FIG. 10B with the axial inverse filter using the incorrect value of β.
Figure 10D:
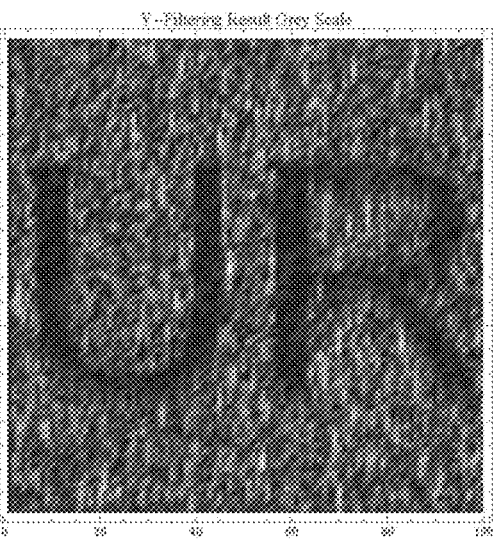
FIG. 10D is an image showing the result of convolution of the image of FIG. 10C with the transverse inverse filter.

The effect of sampling rate is important, and a general trend is illustrated in the following example. A pulse shape of the form of Equation (8) is sampled at exactly twice the modulation frequency in FIG. 8A, along with its pole-zero diagram in FIG. 8B, which indicates the availability of a stable and useful inverse filter. If the sampling rate is doubled, the length of the sampled pulse doubles, as shown in FIG. 9A (increasing the complexity of the solution for the zeros of the Z-transform and then the inverse Z-transform), and the pole-zero diagram demonstrates a similar pattern to the previous example, but with double the number of zeros and a shift towards the unit circle, as shown in FIG. 9B. Continuing along this direction, if we again double the sampling frequency, as shown in FIG. 9C, then the poles double, and once again trend towards the unit circle, as shown in FIG. 9D.

The closest points to the unit circles will correspond to peaks in the frequency response of the inverse filter, producing ringing, poor convergence, and at the limit, instability. Thus, even within the convolution model framework, there is a limit to the degree of superresolution that is achievable with a given asymmetric pulse.

Another issue concerns the sensitivity of the superresolution result to the exact parameters. In practice, even with a well designed transmit pulse and beam, uncertainties and fluctuations within the tissue will create fluctuations in the propagating pulse. So a reconstruction that requires exact parameters would be limited in value. To test that, a convolution with a pulse is performed using one pulse shape and then is inverse filtered using a different parameter. The pulse p[t] was chosen to be of the form of a Gaussian modulated cosine multiplied by $\beta^t$ where $\beta=0.7$. The inverse filter for this was calculated assuming an incorrect $\beta$ of 0.6, other parameters and transverse beam pattern remaining the same. The original scatterers, speckle image, deconvolution in the vertical direction, then full vertical and horizontal directions are given in FIGS. 10A-10D, respectively. While the inverse filter result is no longer a close match to the original scatterer pattern, the UR-shaped voids can still be seen; thus, a degree of superresolution is achieved without the use of exact parameters.

An inverse filter approach has been derived using the Z-transform on stabilized but realizable pulses. Analogous inverse filters may be derived using alternative approaches (Fourier transform, Chirp-Z transform, and others), and other functions besides $\beta^t$ can be utilized to produce stabilized yet practicable pulse shapes. However, the use of the Z-transform and the effect of the beta function in the transform domain are fundamental and illustrative.

A major issue in the use of the inverse filter is the limit of accuracy of the framework. There are a number of contributing factors. The first is the accuracy of the convolutional model compared to the physical world. In particular, the separability of the pulse function into axial and transverse functions is well accepted for the focal region, but not in the near field. However, the increasing use of multiple focus zones and dynamic focus adjustments in imaging systems means that more zones within the image are likely to be represented by a separable function. A second issue is that of noise, since the inverse filter convolves with the additive noise to produce an unwanted term. For inverse filters with poles very close to or on the unit circle, there can be an amplification of the noise near the pole frequencies. Thus, the design of the inverse filter and limiting or suppression of noise are important issues. A third factor is the sampling rate, which in a naïve view could be set very high, leading to arbitrarily fine resolution. That scheme is not practical since higher sampling rates lead to larger polynomials in the Z-transform, more difficult solutions of the polynomial roots and inverses, and more poles in the inverse filter, which will become more difficult to constrain within the unit circle. Thus a practical upper limit will be reached.

Can these asymmetric pulses be produced in practice? In fact it is straightforward to show that the Fourier Transform of the conventional symmetric beam shapes, and those of the asymmetric versions, are reasonably contained within a similar support or bandwidth. That means that a transducer of limited bandwidth can, with some modification of the excitation, produce either the symmetric or the asymmetric (stabilized) version of p(t). For the transverse beam pattern, that means that an aperture with limited support can similarly produce either the symmetric or the asymmetric (stabilized) version of the beam pattern s(x). As an example, consider two functions of x, one a standard Gaussian and the other of the form x times a Gaussian, as shown in FIG. 11A. One is clearly asymmetric, leading to a stable inverse filter. The magnitude of the Fourier transform of both functions is shown in FIG. 11B. The asymmetric function, being more narrow in the x domain, has a greater bandwidth in the transform domain. An imaging system would require a somewhat broader aperture or transducer excitation to achieve the asymmetric function in the lateral or axial dimensions, respectively. Thus, there is some cost associated with realizing pulse shapes that are opportune for inverse filtering and superresolution.

FIG. 12 is a schematic diagram showing an ultrasound system 1 on which the preferred embodiment can be implemented. An ultrasound transducer 3 is attached with ultrasound gel 5 to a body part or other region of interest 7. A processor 9 in communication with the ultrasound transducer 3 performs the operations described above, including control of the ultrasound transducer 3 to produce the appropriate pulse and analysis of the resulting data. The reconstructed image is output to an output 11, which can include one or more of a display, a printer, a persistent storage medium, and an Internet connection to a remote site. The software for the processor 9 can be supplied in any suitable manner, such as a CD-ROM or other persistent storage medium 13.

The result of employing stabilized pulses and their inverse filters is highly beneficial for the imaging of small reflectors or scatterers, and for low-contrast lesion detection in B-scan imaging systems, since the dominant and problematic characteristics of resolution linked to pulse length, and speckle statistics, are eliminated. Instead, resolution is linked to the sampling frequency; for example twice the center frequency of the transducer, leading to an improvement of at least 6-10 times in typical broadband system resolution, more for narrowband systems. Furthermore, the statistics of the solution to the inverse filter resemble the statistics of the actual scatterer distribution, as sampled at the desired sampling frequency. This approach is tractable, can be implemented on most scanning systems, and is adaptable to a wide variety of specific transducers, bandwidths, and applications. Similar considerations apply to other imaging schemes that employ coherent pulses, including OCT systems, and some sonar, radar, and SAR pulse-echo systems. Therefore, the present invention should be construed as limited only by the appended claims.

What is claimed is:

1. A method for forming an image of a region of interest using a pulse-echo imaging device, the method comprising:
    (a) generating a stabilized pulse using the pulse-echo imaging device, the stabilized pulse having a stabilization applied thereto;
    (b) causing the stabilized pulse to be incident on the region of interest to generate a reflected echo;
    (c) receiving the reflected echo in the pulse-echo imaging device;
    (d) applying an inverse filter to the reflected echo, the inverse filter corresponding to the stabilization, to form inverse-filtered echo data; and
    (e) forming an image from the inverse-filtered echo data;
    wherein step (a) comprises generating the stabilized pulse such that all of the zeroes of a Z transform of the stabilized pulse lie within a unit circle.

2. The method of claim 1, wherein the pulse-echo imaging device comprises an ultrasound imaging device.

3. The method of claim 1, wherein the stabilized pulse is an asymmetric stabilized pulse.

4. The method of claim 1, wherein the inverse filter is an inverse Z transform.

5. The method of claim 1, wherein the Z transform of the stabilized pulse has a form $p[n]\beta^n$, wherein $\beta$ is a constant less than one.

6. The method of claim 1, wherein step (a) comprises selecting the stabilization such that the inverse filter suppresses noise in the image.

7. The method of claim 1, wherein the image is a superresolution image.

8. A system for forming an image of a region of interest, the system comprising:
    a pulse-echo imaging device configured to generate a pulse, cause the pulse to be incident on the region of interest to generate a reflected echo, and receive the reflected echo; and
    a processor in communication with the pulse-echo imaging device, the processor configured to control the pulse-echo imaging device to apply a stabilization to the pulse such that the pulse is a stabilized pulse; apply an inverse filter to the reflected echo, the inverse filter corresponding to the stabilization, to form inverse-filtered echo data; and form the image from the inverse-filtered echo data;
    wherein the processor is configured such that all of the zeroes of a Z transform of the stabilized pulse lie within a unit circle.

9. The system of claim 8, wherein the pulse-echo imaging device comprises an ultrasound imaging device.

10. The system of claim 8, wherein the processor is configured such that the stabilized pulse is an asymmetric stabilized pulse.

11. The system of claim 8, wherein the processor is configured such that the inverse filter is an inverse Z transform.

12. The system of claim 8, wherein the processor is configured such that the Z transform of the stabilized pulse has a form $p[n]\beta^n$, wherein $\beta$ is a constant less than one.

13. The system of claim 8, wherein the processor is configured to select the stabilization such that the inverse filter suppresses noise in the image.

14. The system of claim 8, wherein the image is a superresolution image.

15. An article of manufacture for forming an image of a region of interest, the article of manufacture comprising:
    a non-transitory, computer-readable storage medium; and
    code stored on said storage medium, said code, when executed on a processor in communication with a pulse-echo imaging device, controlling the processor for:
    (a) generating a stabilized pulse using the pulse-echo imaging device, the stabilized pulse having a stabilization applied thereto;
    (b) causing the stabilized pulse to be incident on the region of interest to generate a reflected echo;
    (c) receiving the reflected echo in the pulse-echo imaging device;
    (d) applying an inverse filter to the reflected echo, the inverse filter corresponding to the stabilization, to form inverse-filtered echo data; and
    (e) forming the image from the inverse-filtered echo data;
    wherein step (a) comprises generating the stabilized pulse such that all of the zeroes of a Z transform of the stabilized pulse lie within a unit circle.

* * * * *